US 6,531,707 B1

(12) United States Patent
Favreau et al.

(10) Patent No.: US 6,531,707 B1
(45) Date of Patent: Mar. 11, 2003

(54) MACHINE VISION METHOD FOR THE INSPECTION OF A MATERIAL FOR DEFECTS

(75) Inventors: Patrice Favreau, San Leandro, CA (US); Jeffrey Wolinsky, Berkeley, CA (US); Markku E. Jaaskelainen, Sudbury, MA (US)

(73) Assignee: Cognex Corporation, Natick, MA (US)

( * ) Notice: Subject to any disclaimer, the term of this patent is extended or adjusted under 35 U.S.C. 154(b) by 0 days.

(21) Appl. No.: 09/842,842

(22) Filed: Apr. 27, 2001

Related U.S. Application Data

(63) Continuation of application No. 09/750,175, filed on Dec. 29, 2000, now abandoned.

(51) Int. Cl.$^7$ .............................................. G01N 21/88
(52) U.S. Cl. .................. 250/559.46; 356/430; 382/141; 348/125; 348/364
(58) Field of Search .......................... 250/205, 559.45, 250/559.46, 559.01, 559.07, 559.08; 356/429, 430; 382/112, 141; 348/83, 370, 362, 364, 125

(56) References Cited

U.S. PATENT DOCUMENTS

| | | | |
|---|---|---|---|
| 4,779,002 A | * 10/1988 | Takagi et al. | 250/559.22 |
| 5,168,365 A | * 12/1992 | Kawahara | 348/364 |
| 5,281,798 A | * 1/1994 | Hamm et al. | 250/205 |
| 5,347,118 A | * 9/1994 | Iwanaga | 250/205 |
| 5,473,374 A | * 12/1995 | Shimizu et al. | 348/363 |
| 5,559,555 A | * 9/1996 | Shimizu et al. | 348/364 |
| 5,677,733 A | * 10/1997 | Yoshimura et al. | 348/362 |
| 6,195,127 B1 | * 2/2001 | Sugimoto | 348/370 |
| 6,211,505 B1 | * 4/2001 | Nagamatsu | 250/205 |

* cited by examiner

*Primary Examiner*—Stephone B. Allen
*Assistant Examiner*—Eric J Spears

(57) ABSTRACT

A machine vision method and system for inspecting a material. The system comprises a light source arranged to illuminate the material and an imaging device configured to acquire image data corresponding to at least one characteristic of the material while the material is being illuminated by the light source. An image processor is configured to normalize the image data and to control adjustment of an exposure control level for the imaging device based upon the normalized image data. An exemplary method of implementing the machine vision system may include illuminating a material using a light source and obtaining image data corresponding to the material using an imaging device. The image data may be normalized and the adjustment of an exposure control level of the imaging device may be controlled based on the normalized image data.

14 Claims, 8 Drawing Sheets

MACHINE VISION METHOD FOR THE INSPECTION OF A MATERIAL FOR DEFECTS

This is a Continuation of National application Ser. No. 09/750,175 filed Dec. 29, 2000 now abandoned.

BACKGROUND OF THE INVENTION

1. Field of Invention

This invention relates to inspection methods and systems for machine vision applications.

2. Description of Background Information

There are various techniques for inspecting various types of manufactured objects. In such inspections, a determination may be made as to whether the object has certain features—present before or after a given manufacturing step. For example, during manufacturing of continuous web products, such as paper, metals, plastic foils and non-woven materials, the visual quality of the product or product surface may be monitored.

An existing approach for inspection of such products is based on optical measurement using a light source or multiple light sources to illuminate a material to be inspected and a camera to sense visible characteristics of the material to be inspected, such as material integrity or grade of the material. In such systems, camera elements are typically exposed to light transmitted through the continuous web of material or reflected from the surface of the material. In some of these systems, a number of filters may be mechanically switched to adjust or control the exposure control of the camera, which are sometimes referred to as "filter flippers" or "light attenuators".

Existing inspection approaches change the light source or control the light intensity by adjusting the output level in line scan cameras or the pulse duration in matrix cameras.

SUMMARY

An exemplary embodiment of the invention provides A machine vision method and system for inspecting a material. The system comprises a light source arranged to illuminate the material and an imaging device configured to acquire image data corresponding to at least one characteristic of the material while the material is being illuminated by the light source. An image processor is configured to normalize the image data and to control adjustment of an exposure control level for the imaging device based upon the normalized image data.

An exemplary method of implementing the machine vision system may include illuminating a material using a light source and obtaining image data corresponding to the material using an imaging device. The image data is normalized and the adjustment of an exposure control level of the imaging device is controlled based on the raw data.

Other objects, features and advantages of the present invention will become apparent from the following detailed description, the accompanying drawings, and the appended claims.

BRIEF DESCRIPTION OF THE DRAWINGS

The present invention is further described in the detailed description which follows, by reference to the noted drawings by way of non-limiting exemplary embodiments, in which like reference numerals represent similar parts throughout the several views of the drawings, and wherein.

DETAILED DESCRIPTION

Figure 1:
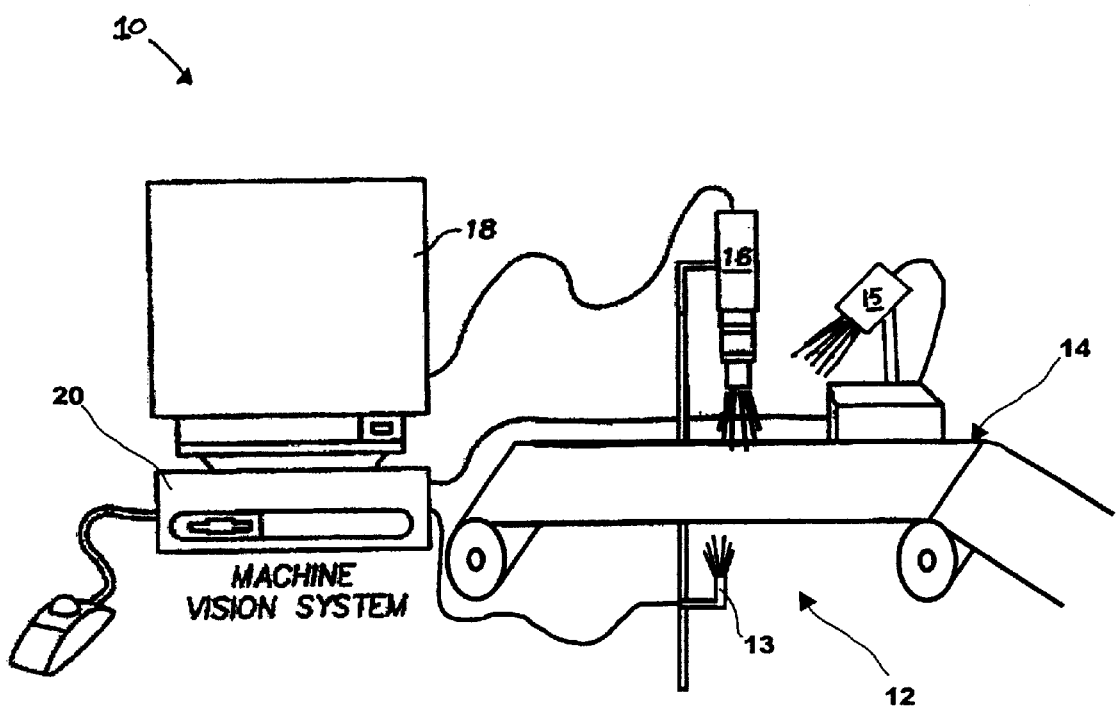
FIG. 1 is an illustrative diagram of an exemplary visual inspection system that can be employed by, for example, a machine vision system for inspecting at least one characteristic of a material, such as a continuous web product having a generally uniform structure, using a set of optical arrangements in an inspection process in accordance with the exemplary embodiment of the invention.

Referring to FIG. 1, in accordance with the present invention, there is provided a visual inspection system that can be employed by, for example, a machine vision system for inspecting at least one characteristic of a material using a set of optical arrangements in an inspection process such as commonly occur in automated manufacturing. For example, the visual inspection system can be employed in a machine vision system 10 for a manufacturing line such as a manufacturing line 12, as shown in FIG. 1.

Using the inspection system, sample-object 14, e.g., a continuous web product or material, can be inspected for compliance with metrics, such as the quantity and size of holes, pits, cracks, streaks, bugs, blister, bumps, splash, grooves, dirt, bubble, ripple, wrinkle, dents, or any other defect optically visible making it less valuable for the user or customer. Such continuous web products may include paper, metals, plastic foils and non-woven materials whereby the visual quality of these products or product surfaces may be monitored.

Image(s) of the sample-object 14 illuminated by a light source 13 is obtained by an imaging device or camera 16. As shown in FIG. 1, the light source may be positioned substantially perpendicular to the sample-object 14, otherwise normal to the sample-object 14 under inspection (i.e., same vantage point as the camera). That way, most of the illumination is reflected back into the camera 16. The light source 13 may be any type of light source, which can illuminate the sample-object.

The camera 16 may be, for example, an analog or CCD (e.g., color) camera, such as a line scan camera or a matrix camera, coupled to the vision system for conversion by the machine vision system 10 to a digital representation of image data, e.g., a pixel representation, corresponding to the continuous web product or material. The machine vision system 10 can include a display monitor 18 or other equipment for displaying the obtained sample-object image to a manufacturing line operator for manual inspection of the sample-object 14. After determining the inspection data of the sample-object 14 under inspection, the machine vision system can provide information about the sample-object's defect position, geometry, size, optical properties, e.g., absolute or normalized intensity, or other characteristics.

In this regard, the machine vision system 10 can provide information about the optical properties or image as an absolute or normalized intensity of the sample-object. These properties may then be used, for example, by a production engineer or other manual inspector, to set or define an exposure control level for the imaging device 16. The exposure control level can determine the amount of illumination that is used by the imaging device 16 to obtain image data corresponding to the sample-object. The exposure control level may be expressed as a percentage of the amount of light used by the imaging device 16. For example, the exposure control level may range from 100%, wherein about 100% of the light emitted from a light source, such as light source 13, is used to obtain image data to 10% wherein about 10% of the light emitted from a light source, such as light source 13, is used to obtain image data.

A normalization level may be set or defined based on the optical properties of the material. Alternatively, the image data may be normalized on a per-pixel basis, for example, by obtaining an average intensity level corresponding to the grade or inspection features of the illuminated sample-object. While obtaining image data, the imaging device 16 may obtain a measured intensity level corresponding to a certain grade or inspection feature of the material, wherein the certain grade or inspection feature of the material is based on the optical properties of the material. The measured intensity level may also correspond to multiple grades or inspection features of the material, which may be based on the optical properties of the material.

The machine vision system 10 may compare the measured intensity level of the material to the average intensity level of the material to control the adjustment of the exposure control level of the imaging device 16. The machine vision system 10 may be used to inspect multiple grades of a continuous web product or material by adjusting the exposure control level of the imaging device based on either the raw level or raw image data.

The machine vision system 10 may be automated or semi-automated. For example, the machine vision system 10 may determine if the sample-object under inspection meets quality control standards with regard to grade or inspection features, etc. These standards can be "taught" to the vision system by way of producing training templates from examples of sample-objects that meet any established visual inspection quality criteria. For example, certain exposure control levels may provide sufficient image intensity regarding certain sample-objects, such as certain grades of continuous web products or materials. The certain exposure control levels may be used to create a template for a certain grade of material. The template for a certain grade of material might set or define the exposure control level at a certain level for that certain sample-object or material. This certain exposure control level may be at 100%, where about 100% of the light emitted a light source is used to obtain image data. Image data can then be normalized, for example, to obtain an average intensity level based on that certain sample-object or material, such as a certain grade of that material.

The machine vision system 10 can then compare a measured intensity value of a questionable sample-object under inspection against the average intensity level of the pre-trained templates in some manner to determine if the sample-object satisfies the inspection criteria without the presence or input of a manufacturing line operator. If the sample-object does not satisfy the inspection criteria, i.e., the measured intensity level differs from the raw intensity level by a predetermined amount, the exposure control level of the imaging device 16 may be adjusted.

In this regard, if the vision system 10 ascertains that a sample-object under inspection does not meet the standard, an image processor 20 as shown in FIG. 1, connected to the vision system 10, can be signaled to control the adjustment of the exposure control level of the imaging device 16. The image processor might adjust the exposure control level such that the measured intensity level is equal to or differs from the raw intensity level by an acceptable amount.

Alternative object inspection and manipulation functions can be provided in a manufacturing line or web-based machine vision system like that of FIG. 1.

Different regions on continuous web products or materials may respond differently to being illuminated by a light source, i.e., having different intensity levels. For example, one grade of the continuous web product or material may respond differently to illumination than does another grade of the continuous web product or material.

In the illustrated embodiment, the image data corresponding to the sample-object or a surface of the sample-object may change between different exposure control levels or as the sample object travels along a manufacturing line such as a manufacturing line 12, as shown in FIG. 1. Acceptable exposure control levels of the imaging device 16 may be based on raw image data, which may be continuously normalized to compensate for variations in light intensity thereof such that an average intensity level can be obtained on a static or adaptive normalization level. The static normalization level may be predetermined through historical data and the adaptive normalization level continuously normalizes a portion of the raw image data.

The image data includes a plurality of pixels which correspond to the sample-object or material being inspected, such as, for example, digital data from the imaging device 16. A normalizer may be applied to each pixel to produce a flat-line toward a "target value" of the sample-object or material for that particular pixel. The normalizer may be an inverse function of each pixel, which when multiplied with the intensity value of each pixel, produces the flat-line toward the "target value" of the sample-object or material for that particular pixel.

The target value may be represented by a value ranging from 0 to 255, but it may be preferable to limit the target value to a range of 20 to 240 so that both bright and dark defects can be detected. For example, if the target value is set at 255, a bright defect could not be detected since the target is already at its maximum intensity value. Similarly, dark defects could not be detected if the target value was set at 0 since the target is already at its minimum intensity value.

In the illustrated embodiment, the normalizer multiplier is a value between 0 and 16383, however, the normalizer multiplier may be any value that can be used to produce a flat-line or an average intensity level of the image data corresponding to the sample-object or material for each particular pixel.

The normalizer may adapt to a dynamic range or working range, such as, for example, ranging from 16 to 1. This working range may be extended at least in part by the exposure control level. The exposure level control can scale the raw image data for the normalizer, which improves inspection capabilities of the machine vision system 10 when the optical properties (e.g., reflectivity or transmissivity) of the material change significantly. Therefore, as the optical properties change in the sample-object or material, e.g., the grade of the material changes, the normalizer may adapt to an optimum working range to effectively normalize the image data, for example, by obtaining an average of the maximum raw intensity levels or target intensity value of the material and comparing that average raw intensity level against a measured intensity level of the material. Then measured intensity levels of the material for each pixel can be normalized from the average raw intensity level for each pixel, or the "target value" of the material.

The normalized image data includes a plurality of pixels having a range of intensity values, for example 0 to 255. The adjustment of the exposure control level is controlled by comparing an average of the maximum measured raw intensity level for each pixel of the sample-object and the target of the maximum raw intensity level for each pixel of the sample-object inside the region of interest.

If the average of the maximum measured raw intensity level for each pixel of the image data corresponding to a sample-object or material is equal to the target of the maximum raw intensity level for each pixel of the image data then the exposure time of the imaging device will not be changed, i.e. the exposure time is correct for that particular area of interest. However, if the average of the maximum measured raw intensity level for each pixel of the sample-object or material is less than the target of the maximum raw intensity level for each pixel then the exposure time of the imaging device will be increased. Alternatively, the exposure control level may be decreased, for example, from 70% to 50% while the exposure time remains constant. Likewise if the average of the maximum measured raw intensity level for each pixel of the sample-object or material is greater than the target of the maximum raw intensity level for each pixel then the exposure time of the imaging device will be decreased. Alternatively, the exposure control level maybe increased, for example, from 50% to 70% while the exposure time remains constant.

Generally, intensity values of the pixels range from 0 to 255 and normalization of the image data may normalize all the intensity values to be within the 0 to 255 range.

In one embodiment, an output of image data can be used to classify pixels as having an acceptable intensity level using the exposure control level and as having an unacceptable intensity level using the exposure control level, whereby the exposure control level needs adjustment. In such an implementation, the measured intensity levels of the material for each pixel may be compared with a threshold or average intensity level, e.g., some intensity level that has been predetermined to correspond to a level associated with, for example, a certain grade of the material. Thus, making the image of the sample-object or material primarily a binary image.

Other image processing, for example, various methods of subtraction, may be used to normalize the difference image data. Normalization may be used to compensate for Photo Response Non-Uniformity (PRNU), sensitivity variation, light variation, lens distortion, sensor deviation and long term variation of sample-objects, materials or the imaging device, such as a CCD camera.

Figure 2:
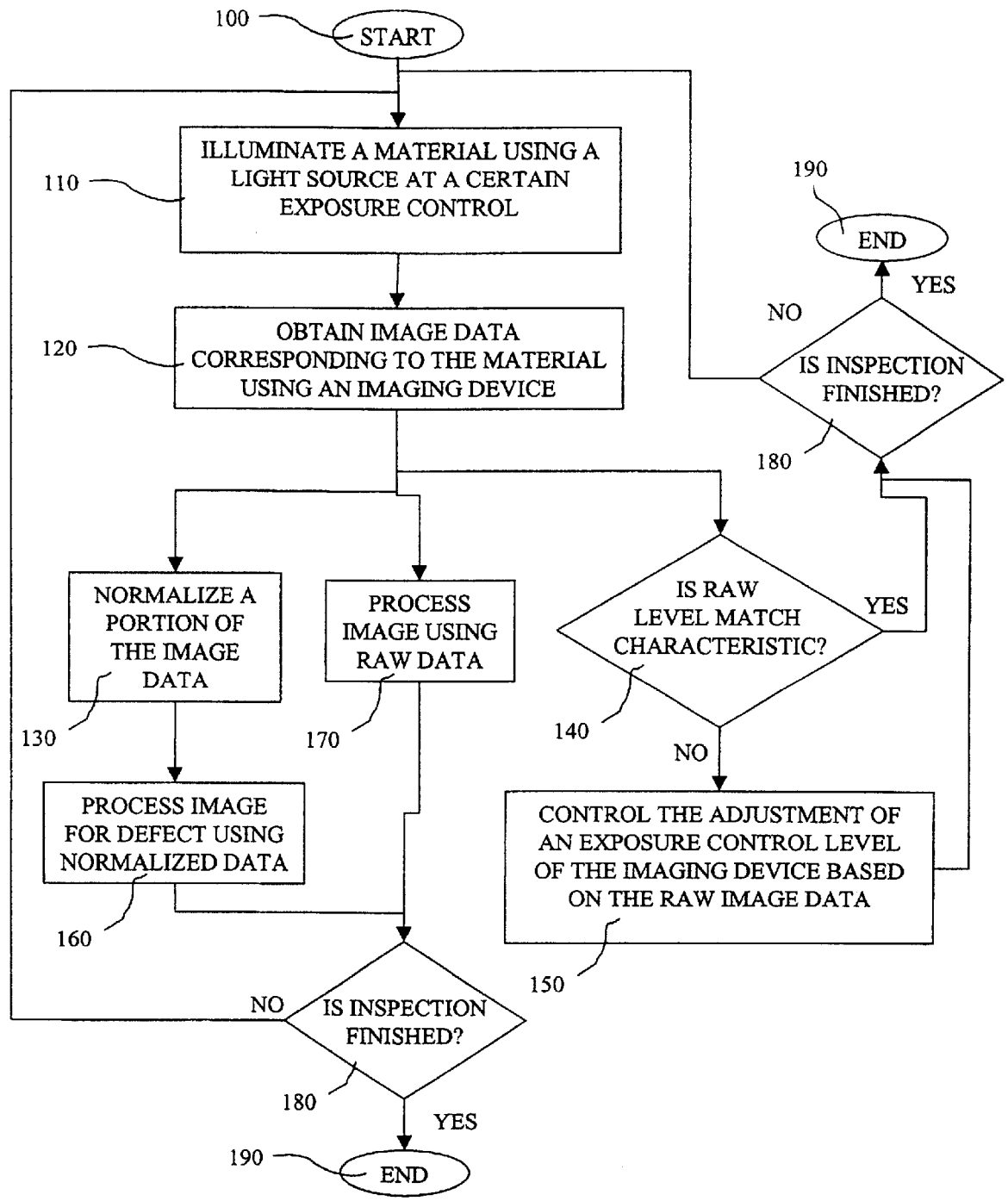
FIG. 2 is a flow chart illustrating a method designed in accordance with a first exemplary embodiment of the invention in which a material, such as a continuous web product or material, is inspected for at least one characteristic of the material using a set of optical arrangements.

FIG. 2 is a flow chart illustrating a method designed in accordance with a first exemplary embodiment of the invention in which a material, such as a continuous web product, is inspected for at least one characteristic of interest, for example, its grade or other inspection feature. The method begins at 100 and control proceeds to 110, at which a material, for example a continuous web product, is illuminated with a light source at a certain exposure control. Control then proceeds to 120, at which image data corresponding to an image of the material is obtained using an imaging device and control proceeds to 130, 140 and 170. At 130, a portion of the raw image data is normalized and control proceeds directly to 160, at which the normalized image data is processed to detect defects in the sample-object or material through image processing, such as, for example, using image processor 20. Control then proceeds to 180.

At 140, a determination is made whether an average of the maximum measured raw intensity levels of the material equals a target value of the maximum raw intensity values of the material. If so, control proceeds to 120. If not, control proceeds to 150. At 150, the adjustment of an exposure control of the imaging device is controlled based on the raw image data upon which the determination at 140 was made. If the average of the maximum measured intensity levels of the material is less than the target value of maximum raw intensity levels of the material then the exposure time of the imaging device will increased. At 170, the raw image data is processed, for example, using image processor 20 so as to view the material in real time, for example, using display 18, or for edge inspection, such as edge tracking. After 150, 170, control proceeds to 180. At 180, a determination is made whether inspection is finished. If not, control proceeds to 110. If so, control proceeds to 190, at which the method ends.

Figure 3:
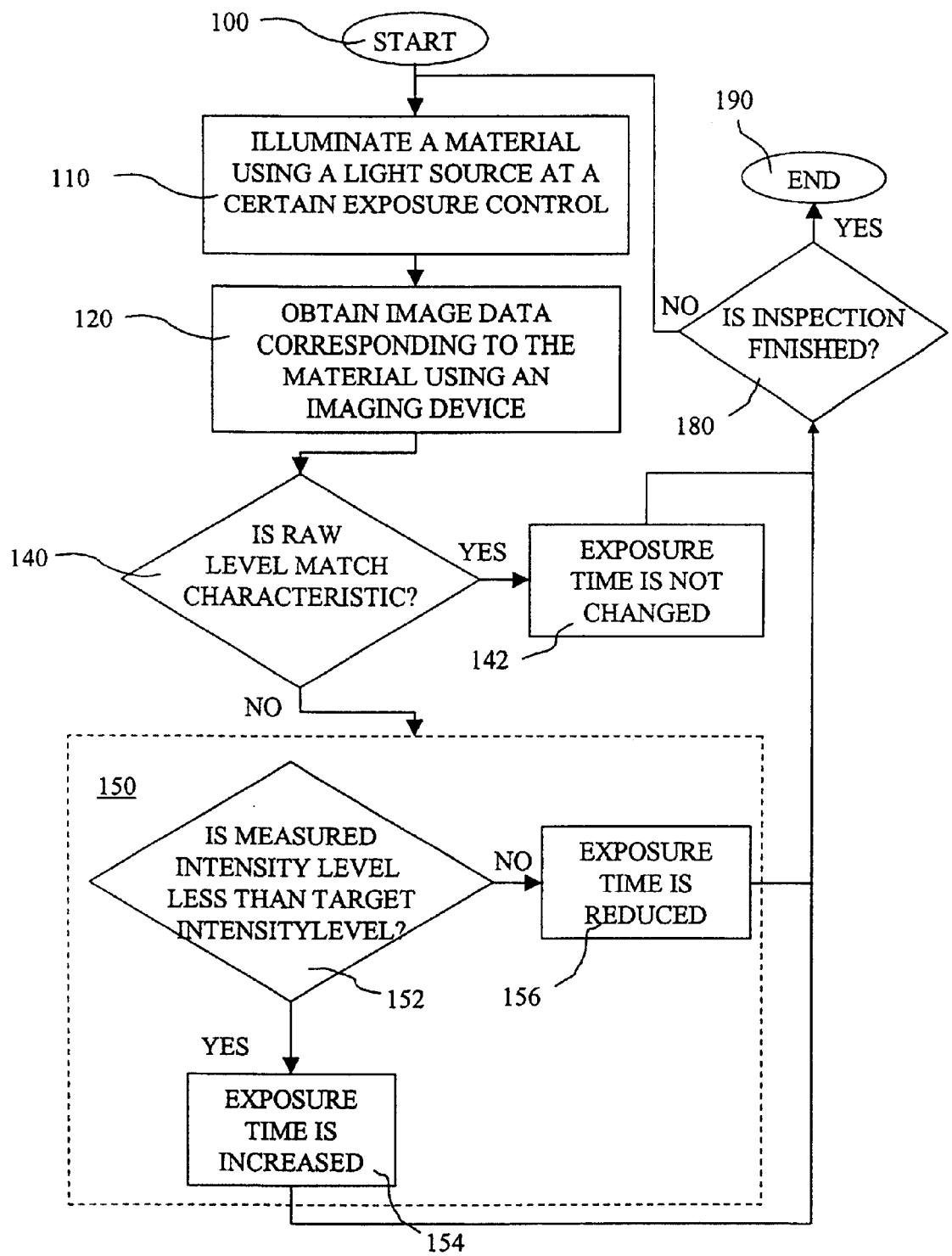
FIG. 3 is a flow chart showing the method of FIG. 2 in greater detail.

FIG. 3 shows a flow chart that describes certain portions of the above method in greater detail while not showing other portions. For example, as stated above, the method begins at 100 and control proceeds to 110, at which a material, for example a continuous web product, is illuminated with a light source at a certain exposure control. Control then proceeds to 120, at which image data corresponding to an image of the material is obtained using an imaging device and control proceeds to 140. At 140, a determination is made whether an average of the maximum measured raw intensity levels of the material equals a target value of the maximum raw intensity values of the material. If so, control proceeds to 142, at which the exposure control of the imaging device is not adjusted and the exposure time is not changed and control then proceeds to 180. If not, control proceeds to 152. At 152, a determination is made whether the average of the maximum measured intensity level of the raw image data is less than the target intensity value of the material. If so, control proceeds to 154, at which the exposure control level of the imaging device is adjusted to increase the exposure time and control then proceeds to 180. If not, control proceeds to 156, at which the exposure control of the imaging device is adjusted to decrease the exposure time. Control then proceeds to 180, at which a determination is made whether inspection is finished. If not, control proceeds to 110. If so, control proceeds to 190, at which the method ends.

Figure 4:
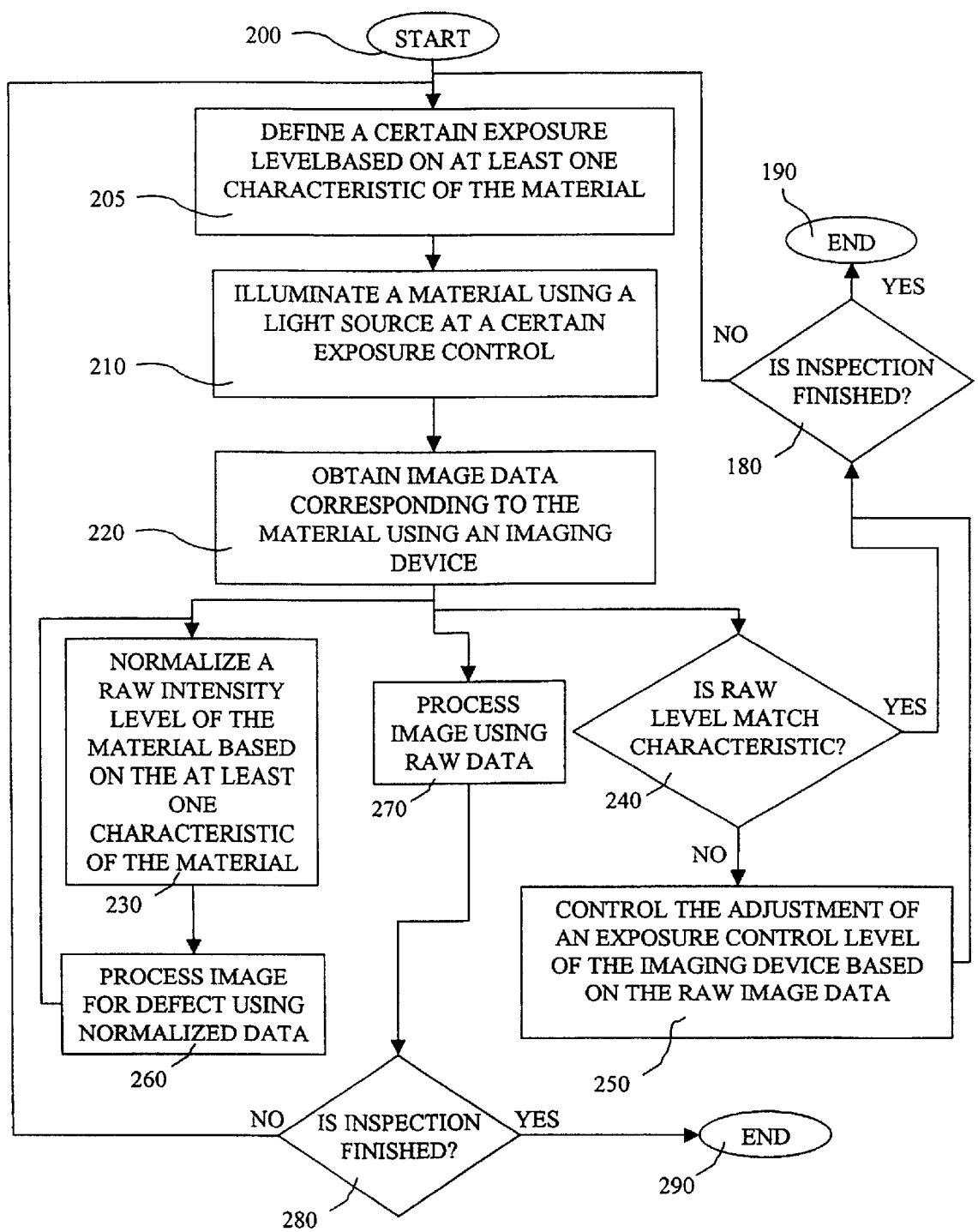
FIG. 4 is a flow chart illustrating a method designed in accordance with a second exemplary embodiment of the invention in which a material, such as a continuous web product or material, is inspected for at least one characteristic of the material using a set of optical arrangements.

FIG. 4 is a flow chart illustrating a method designed in accordance with a second exemplary embodiment of the invention in which a material, such as a continuous web material, is inspected for at least one characteristic of the material, using a set of optical arrangements. The method begins at 200 and control proceeds to 205. At 205, a certain exposure level based on at least one characteristic of the material is defined, for example, by a product engineer or other manual inspector. Control then proceeds to 210, at which a material, for example a continuous web product, is illuminated with a light source at the certain exposure level. Control then proceeds to 220, at which image data corresponding to an image of the material is obtained using an imaging device and control proceeds to 230, 240 and 270. At 230, a portion of the raw intensity level of the material is normalized based on at least one characteristic of the material and control proceeds directly to 260. At 260, the normalized image data is processed to detect defects in the sample-object or material through image processing, such as, for example, using image processor 20. Control then proceeds to 230 such that the method employs continuous normalization of a portion of the raw image data until inspection is finished.

At 240, a determination is made whether a measured intensity value of the raw image data equals an average of the maximum raw intensity values of the material. If so, control proceeds to 242, at which the exposure control of the imaging device is not adjusted and the exposure time is not changed. Control then proceeds to 220. If not, control proceeds to 250. At 250, the adjustment of an exposure control of the imaging device is controlled. For example, if the average of the maximum measured intensity value of the raw image data is less than the target of the maximum raw intensity values of the material then the exposure time of the imaging device will be increased. Control then proceeds to 220. At 270, some of the raw image data is used for image processing, such as to view the material in real time via the raw image data is processed, for example, using image processor 20 so as to view the material in real time, for example, using display 18, or for edge inspection, such as edge tracking. After 250, 270, control proceeds to 280, at which a determination is made whether inspection is finished. If not, control proceeds to 205. If so, control proceeds to 290, at which the method ends.

Figure 5:
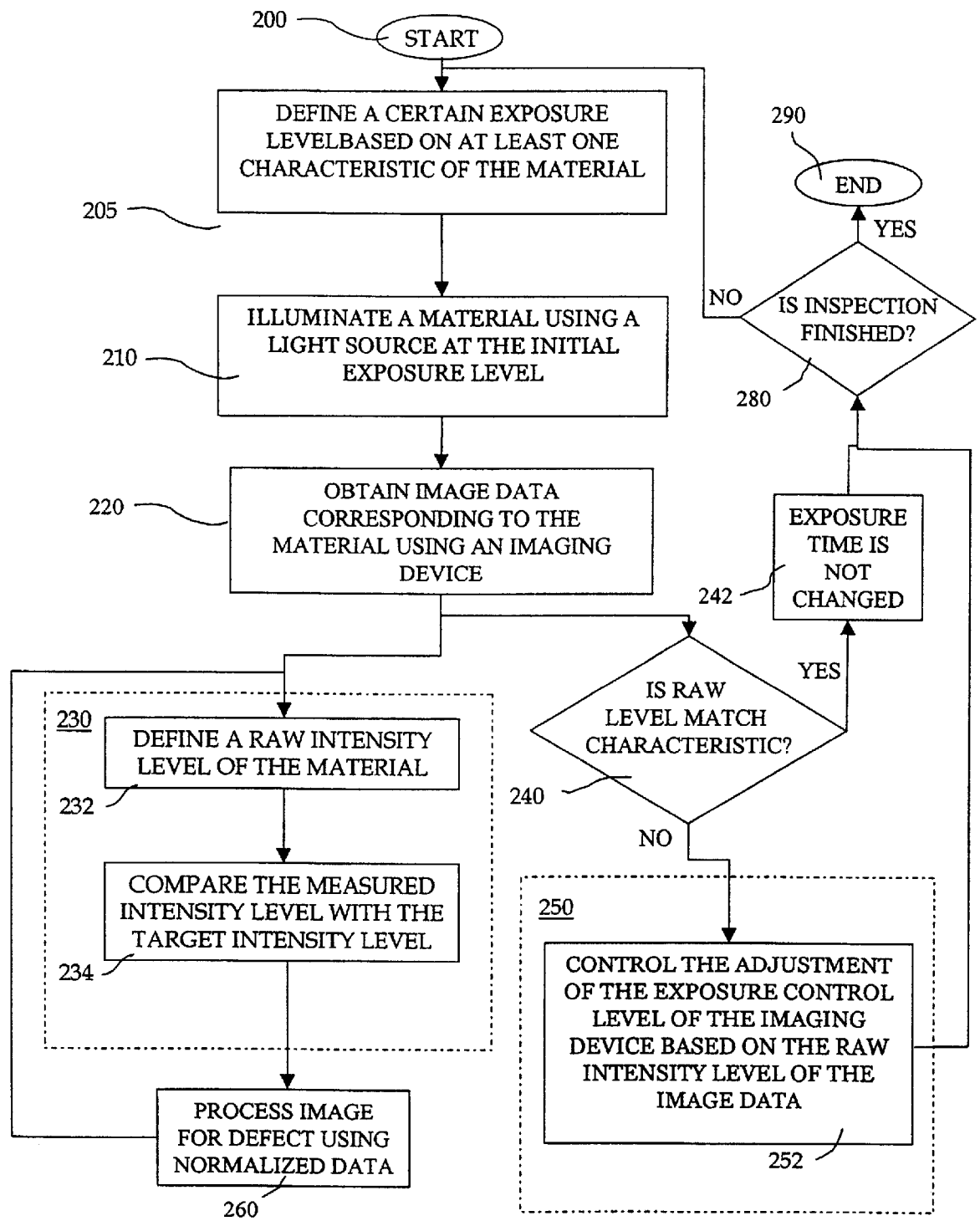
FIG. 5 is a flow chart showing the method of FIG. 4 in greater detail.

FIG. 5 shows a flow chart that describes certain portions of the above method in greater detail while not showing other portions. For example, the method begins at 200 and control proceeds to 205. At 205, a certain exposure level based on at least one characteristic of the material is defined, for example, by a product engineer or other manual inspector. Control then proceeds to 210, at which a material, for example a continuous web product, is illuminated with a light source at the certain exposure level. Control then proceeds to 220, at which image data corresponding to an image of the material is obtained using an imaging device and control proceeds to 232 and 240. At 232, a raw intensity of the material is defined, i.e., a target intensity value for the normalized data obtained by normalizing the raw image data. Control proceeds to 234, at which a measured intensity level of the raw image data is compared with the average intensity value of the raw intensity level. Control then proceeds directly to 230, such that the method employs continuous normalization of a portion of the raw image data. At 240, a determination is made whether a measured intensity value of the raw image data equals an average of the maximum raw intensity values of the material. If so, control proceeds to 242, at which the exposure control of the imaging device is not adjusted and the exposure time is not changed. Control then proceeds to 280. If not, control proceeds to 252. At 252, the adjustment of an exposure control of the imaging device is controlled based on the raw intensity level of the image data. For example, if the measured intensity value of the raw image data is greater than the average of the maximum raw intensity values of the material then the exposure time of the imaging device will be decreased. Control then proceeds to 280, at which a determination is made whether inspection is finished. If not, control proceeds to 205. If so, control proceeds to 290, at which the method ends.

Figure 6:
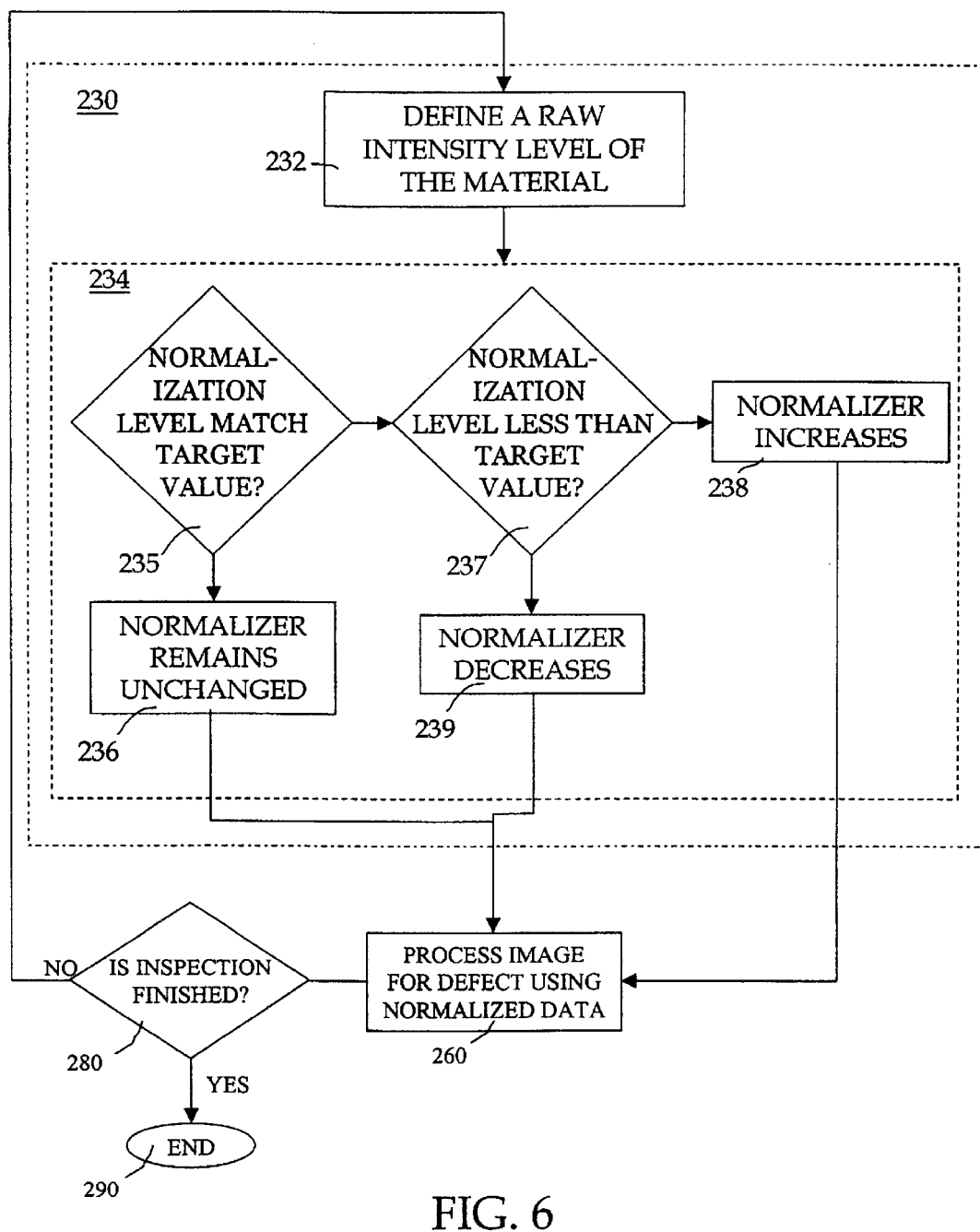
FIG. 6 is a flow chart showing the method of FIG. 5 in greater detail.

FIG. 6 shows a flow chart that describes the above-described normalization of a portion of the raw intensity level of the material in greater detail. For example, at 232, a normalization level of the material is defined, i.e., a target intensity value for the normalized data obtained by normalizing the raw image data. Control proceeds to 234, at which the measured intensity level of the raw image data is compared with the target intensity value of the material. Control then proceeds to 235. Specifically, at 235, a determination is made whether the measured intensity level of the material is equal to the target intensity value. If so, control proceeds to 236, at which the normalization level remains unchanged and control proceeds directly to 260. If not, control proceeds to 237, at which a determination is made whether the measured intensity level of the material is less than the target intensity value. If so, control proceeds to 238, at which the normalization level is increased and control then proceeds to 260. If not, control proceeds to 239, at which the normalization level is decreased. For example, the normalization level may be, for example, a normalization multiplier value obtained by multiplying the inverse of the normalization level by the normalization multiplier value to obtain a flat-line on a per-pixel basis. Control then proceeds directly to 260.

At 260, the normalized image data is processed to detect defects in the sample-object or material through image processing, such as, for example, using image processor 20. Control then proceeds to 280, at which a determination is made whether inspection is finished. If not, control proceeds to 230 such that the method employs continuous normalization of a portion of the raw image data until inspection is finished. If so, control proceeds to 290, at which the method ends.

In the above-described method, the normalization level and the exposure control level may be set at the same or different times. Normalization may occur at the same time as controlling the adjustment of the exposure control level.

Various normalization techniques, which may normalize the image data, after the image data has been generated but before feature inspection is performed on the difference image data may be implemented with the machine vision system 10. For example, normalization may be performed by using subtraction, multiplication or other normalization techniques as well.

In each of the above-described methods, the exposure control levels and the normalization levels may be ascertained from historical image data corresponding to the material or sample-object and may be manual, semi-automated, or automated in nature. Alternatively, the initial exposure control level may be arbitrarily set in the second exemplary embodiment.

Figure 7:
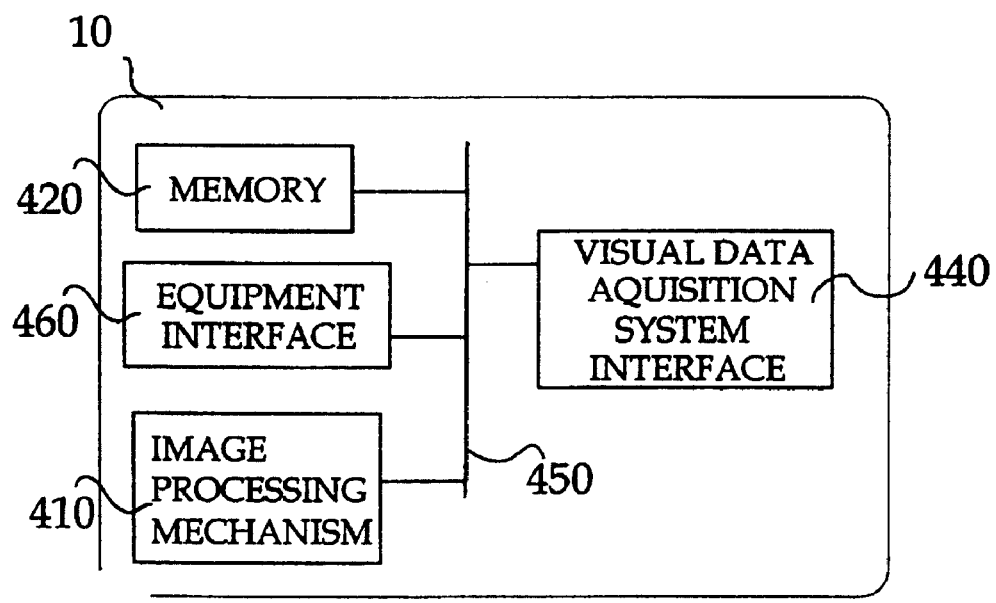
FIG. 7 is an illustrative diagram of the elements of the visual inspection system illustrated in FIG. 1.

FIG. 7 is a functional block diagram of one implementation of the machine vision system 10 illustrated in FIG. 1. As shown in FIG. 7, the machine vision system 10 may include a image processing mechanism 410, a memory 420, a visual data acquisition system interface 440, a communication/data/control bus 450 and an equipment interface 460. The communication/data/control bus 450 couples elements 410, 420, 440 and 460 together and allows for cooperation and communication between those elements.

The memory 420 may be implemented with, for example, a sufficient quantity of RAM, e.g., 32,64,96 or 128 megabytes.

The visual data acquisition system interface 440 may include both hardware and software to allow the system 10 to communicate with a visual data acquisition system, which may include, for example, camera 16 illustrated in FIG. 1.

Image processing mechanism 410 may fetch instructions from memory 420 and decode them, which may cause the image processing mechanism 410 to transfer data to or from memory 420 or to work in combination with the equipment interface 460 (for example, to input or output information), or the visual data acquisition system interface 440 (for example, to input image-data from or output instructions to the visual data acquisition system)

In cases where the machine vision system 10 is automated, either fully or partially, the equipment interface 460 may include, for example, software for cooperating with the image processing mechanism 410 or other inspection tools used in such object inspection to determine if a sample-object satisfies inspection criteria. If the sample-object 14 is deemed satisfactory, the exposure control level of the imaging device 16 might remain unchanged while another determination might control the adjustment of the exposure control level of the imaging device 16 based on the raw intensity level of the material.

Figure 8:
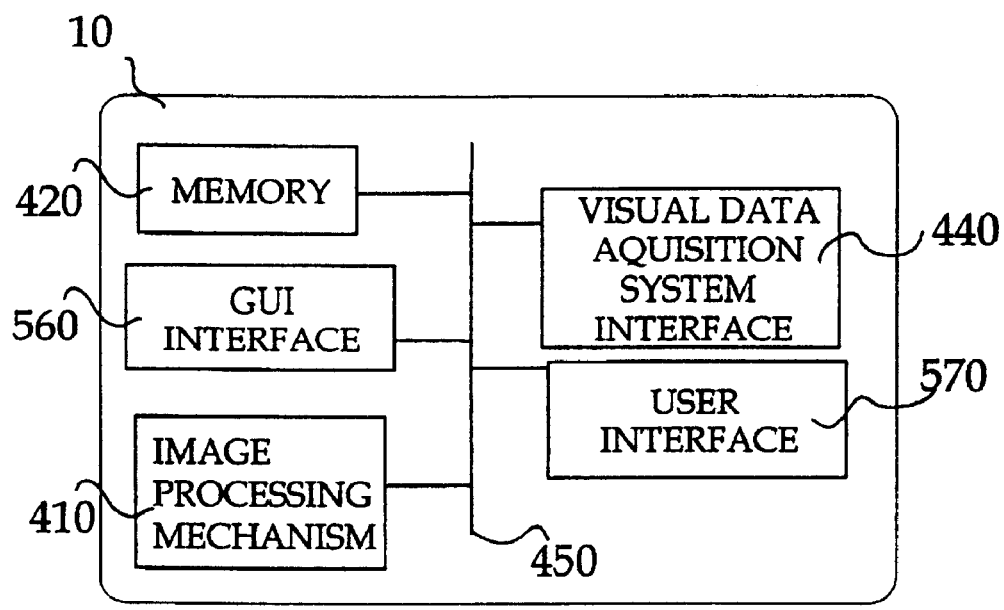
FIG. 8 is an illustrative diagram showing a modification of the visual inspection system illustrated in FIG. 7.

FIG. 8 is a functional block diagram of another implementation of the machine vision system 10 illustrated in FIG. 1. As shown in FIG. 8, the machine vision system 10 may include a image processing mechanism 510, the memory 420, a visual data acquisition system interface 440, the communication/data/control bus 450, a GUI interface 560 and a user interface 570. The communication/data/control bus 450 couples elements 510, 420, 440, 560 and 570 together and allows for cooperation and communication between those elements.

Image processing mechanism 510, similarly to image processing mechanism 410, may fetch instructions from memory 420 and decode them, which may cause the image processing mechanism 510 to transfer data to or from memory 420 or to work in combination with the GUI interface 560 (for example, to provide inspection information to the user via, for example, the display 18).

The user interface 570 may include, for example, hardware and software for cooperating with the display 18, a keyboard and mouse, etc. Moreover, the user interface 570 may include a speaker and microphone, not shown, for outputting and inputting information to and from a user, such as an initial exposure control level. The user interface 570 may operate in conjunction with the image processing mechanism 510 to allow a user to interact with software programs stored in the memory 420 and used by the image processing mechanism 510 so as to perform the operations illustrated in FIGS. 2–6.

The GUI interface 560 and the user interface 570 may be implemented in machine vision systems 10 that manually inspect sample-objects 14. A manufacturing line operator, for example, may determine if a sample-object satisfies inspection criteria and may input data, such as an initial exposure control level or a normalization level into the machine vision system 10 via GUI interface 560 and the user interface 570 based on his/her determinations. One determination might keep the exposure control level unchanged while another determination might control the adjustment of the exposure control level of the imaging device 16 based on the normalization level of the material or on the normalized image data.

Hence, it is within the principles of the present invention for the machine vision system 10 to be operated to manually inspect sample-objects (as illustrated shown in relation to FIG. 7) or to be operated in an automated fashion, either in full or in part, to inspect sample-objects (as illustrated in relation to FIG. 8).

The processing performed by each of the image processing mechanisms 410, 510 and the machine vision system 10 may be performed by a general purpose computer alone or in connection with a specialized image processing computer. Such processing may be performed by a single platform or by a distributed processing platform. In addition, such processing and functionality can be implemented in the form of a special purpose hardware or in the form of software being run by a general purpose computer or any combination of both. Any data handled in such processing or created as a result of such processing can be stored in any memory as is conventional in the art. By way of example, such data may be stored in a temporary memory, such as in the RAM of a given computer system or subsystem. In addition, or in the alternative, such data may be stored in longer-term storage devices, for example, magnetic disks, rewritable optical disks, and so on. For purposes of the disclosure herein, a computer-readable media may comprise any form of data storage mechanism, including such existing memory technologies as well as hardware or circuit representations of such structures and of such data.

While the exemplary embodiment describes optical properties, e.g., reflectivity properties and/or transmissivity properties, that may be used for one application, e.g., continuous web products or materials, the exposure control levels or the normalization levels may be based on other optical properties of the material or sample-object as well. Other optical properties or behaviors may be used for applications other than continuous web products or materials.

Lighting states can be any combination of illumination in each image. Although the exemplary embodiments have been described hereinabove with only one light source, it may be possible for the background lighting and/or ambient lighting from the manufacturing facility to contribute to the image data. However, the light source may be positioned substantially closer to the sample-object than the background and/or ambient lighting. Therefore, the contribution from both the background and/or ambient lighting may be so small and irrelevant to the image that both background and/or ambient lighting can be ignored.

While the invention has been described with reference to certain illustrated embodiments, the words which have been used herein are words of description rather than words of limitation. Changes may be made, within the purview of the appended claims, without departing from the scope and spirit of the invention is its aspects. Although the invention has been described herein with reference to particular structures, acts and materials, the invention is not to be limited to the particulars disclosed, but rather extends to all equivalent structures, acts, and materials, such as are within the scope of the appended claims.

What is claimed is:

1. A method comprising:

illuminating a material using a light source, the material having at least one characteristic;

obtaining image data corresponding to the material using an imaging device;

normalizing the image data to provide normalized image data;

processing the normalized image data to detect defects in the material; and controlling the adjustment of an exposure control level of the imaging device based on the image data.

2. The method of claim 1, wherein the exposure control level is set based on the at least one characteristic of the material.

3. The method of claim 1, the at least one characteristic of the material indicates a grade of the material.

4. The method of claim 1, the at least one characteristic of the material indicates multiple grades of the material.

5. The method of claim 1, wherein obtaining image data comprises setting an initial exposure control level of the imaging device for the material based on the at least one characteristic of the material.

6. The method of claim 1, wherein obtaining image data comprises obtaining a measured intensity level based on the at least one characteristic of the material.

7. The method of claim 1, wherein normalizing the image data implements adaptive normalization or static normalization.

8. The method of claim 1, wherein normalizing the image data comprises obtaining an average intensity level based on the at least one characteristic of the material.

9. The method of claim 8, wherein controlling the adjustment of the exposure control level comprises comparing a measured intensity level of the material to the average intensity level of the material.

10. The method of claim 1, wherein the at least one characteristic of the material is determined based on optical properties of the material.

11. The method of claim 10, wherein the optical properties include reflectivity properties, transmissivity properties, or reflectivity and transmissivity properties.

12. A method for inspecting multiple grades of a material, comprising:

illuminating a material using a light source;

obtaining image data corresponding to the multiple grades of the material using an imaging device, a certain grade of the material being used to define an exposure control level;

normalizing the image data;

processing the normalized image data to detect defects in the material; and controlling the adjustment of the exposure control level of the imaging device based on the image data.

13. The method of claim 12, wherein normalizing the image data implements adaptive normalization or static normalization.

14. The method of claim 12, wherein the adjustment of the exposure control level is optional.

* * * * *